(12) United States Patent
Scharmach

(10) Patent No.: US 10,295,452 B2
(45) Date of Patent: May 21, 2019

(54) PHOTOMETER/NEPHELOMETER DEVICE AND METHOD OF USING TO DETERMINE PROPPANT CONCENTRATION

(71) Applicant: William J. Scharmach, Grand Island, NY (US)

(72) Inventor: William J. Scharmach, Grand Island, NY (US)

(73) Assignee: PRAXAIR TECHNOLOGY, INC., Danbury, CT (US)

(*) Notice: Subject to any disclaimer, the term of this patent is extended or adjusted under 35 U.S.C. 154(b) by 653 days.

(21) Appl. No.: 15/004,023

(22) Filed: Jan. 22, 2016

(65) Prior Publication Data

US 2017/0212029 A1    Jul. 27, 2017

(51) Int. Cl.

| | |
|---|---|
| *E21B 43/267* | (2006.01) |
| *C09K 8/80* | (2006.01) |
| *G01N 15/06* | (2006.01) |
| *E21B 43/26* | (2006.01) |
| *G01N 21/53* | (2006.01) |
| *G01N 21/85* | (2006.01) |

(52) U.S. Cl.
CPC ............ *G01N 15/06* (2013.01); *E21B 43/26* (2013.01); *E21B 43/267* (2013.01); *G01N 21/53* (2013.01); *G01N 21/85* (2013.01); *G01N 2015/0693* (2013.01)

(58) Field of Classification Search
CPC ... C09K 8/805; C09K 2208/00; E21B 47/123; E21B 43/267; E21B 43/26
See application file for complete search history.

(56) References Cited

U.S. PATENT DOCUMENTS

| | | |
|---|---|---|
| 3,657,532 A | 4/1972 | Zimerman |
| 4,618,939 A | 10/1986 | Davis |
| 4,779,186 A | 10/1988 | Handke et al. |
| 8,997,860 B2 | 4/2015 | Freese et al. |
| 2005/0263281 A1* | 12/2005 | Lovell ............... E21B 47/123 166/255.1 |
| 2010/0022435 A1 | 1/2010 | Henning et al. |
| 2011/0214488 A1 | 9/2011 | Rose et al. |
| 2014/0061449 A1 | 3/2014 | Tunheim et al. |
| 2015/0015884 A1 | 1/2015 | Russell et al. |
| 2015/0060065 A1 | 3/2015 | Scharmach et al. |
| 2016/0009582 A1* | 1/2016 | Heimel ............... C02F 9/00 210/638 |

* cited by examiner

*Primary Examiner* — Zakiya W Bates
(74) *Attorney, Agent, or Firm* — Iurie A. Schwartz

(57) ABSTRACT

A system that provides for the measurement and control of proppant concentration in a liquefied gas fluid stream utilizing a non-nuclear optical detection device such as a near-infrared (NIR), visible (Vis), and ultraviolet (UV) photometer/nephelometer to be used in the fracture treatment of subterranean hydrocarbon formations.

16 Claims, 3 Drawing Sheets

PHOTOMETER/NEPHELOMETER DEVICE AND METHOD OF USING TO DETERMINE PROPPANT CONCENTRATION

FIELD OF INVENTION

The present invention relates to a control system and method utilizing a non-nuclear optical detection device such as a near-infrared (NIR), visible (Vis), and ultraviolet (UV) photometer to regulate the flow of proppant into a fracture treatment fluid stream.

BACKGROUND OF THE INVENTION

Hydraulic fracturing as utilized herein refers to a process whereby a fluid is pumped into a well bore communicating with a subterranean reservoir under sufficient pressure to fracture the matrix of the subterranean geological formation. As these pressure forces increase, they commence and propagate fractures (fissures or cracks) in the reservoir matrix. The dimensions of the fractures generally increase by continuing to pump the pressurized fluid into the formation through the well bore.

Proppant is typically added to prop the fractures open and facilitate oil and gas recovery from the well after the treatment has been completed. The materials generally comprise of treated sands and man-made ceramics with specific gravities of 2.5 to 3.5. In order for a fracturing treatment to be effective and allow the flow of oil and gas from a reservoir to a well, proppant must be distributed in a manner that is conducive to improving the conductivity between the payzone and the wellbore.

Conventional hydraulic fracturing fluids consist of water or water-based fluids utilizing thickening agents or gels to aid in proppant transport so that it can sufficiently transport the proppant within the fracture. For low viscosity fluids like $CO_2$, proppant transport is limited, in one respect, due to the lack of additive systems available that may enhance viscosity and improve the proppant carrying capacity of the fluid.

Utilization of liquid carbon dioxide ($LCO_2$) in fracture treatment of oil and gas formations is well known and has certain advantages in water sensitive and low pressure formations. First, the use of $LCO_2$ enables a significant reduction in water volume utilized, which minimizes formation damage caused by the water and second, it promotes water flow-back (i.e., retrieval of water introduced, or produced, in the fracture treatment) through expansion when pressure is let off the fractured formation. However, with a predominantly $LCO_2$ fracturing fluid, a major drawback exists because of the less than optimal proppant transport characteristics of this fluid resulting in poor placement of proppant.

Ultra-light weight proppants (ULWP) materials have been developed to combat transport issues in thin fluids through a reduced material density. These proppants generally have specific gravities ranging from ~1 to 2. Proppants with specific gravity close to 1 are especially useful as their transport mimics that of the carrier fracturing fluid. These proppants, however, are undetectable by a nuclear densitometer, a common device used in fracturing operations to detect proppant concentrations. A difference in density between the proppant and the carrier fluid is required in order for the proppant concentration to be measured by the nuclear densitometer.

For example, U.S. Pat. Nos. 3,657,532 and 4,618,939 disclose the use of nuclear densitometers for non-intrusive and continuous measurement of densities of flowing fluids or slurries. Typically, these instruments include a gamma radiation source. The radiation is high frequency, high energy, and exhibits a high penetration depth with a wavelength on the order of $10^{-12}$ meters (smaller than the diameter of an atom). This allows emitted photons to pass through treatment piping and reach the detector. Gamma ray attenuation (by absorption and scattering) occurs at the atomic and subatomic level. As a result, gamma attenuation is dependent on:

atomic number and density of material it is passing through, & the
 thickness of the material.

The attenuation of gamma rays is proportional to the density material. Meaning materials having a relatively high density (e.g. lead, bismuth, and tungsten) are able to absorb gamma radiation more easily than materials with a lower density (e.g. aluminum, plastics). For treatment fluids containing proppant, the detection of solids is made possible by the proppants density being of 2 to 4 times greater than that of the carrier fluid. Consequently, for proppant materials with a density close to that of the carrier fluid such as ULWP (i.e., specific gravity of close to 1) detection by a nuclear densitometer is not possible.

For control of proppant concentration in the fracturing treatment fluid stream, generally the densitometer is used as a feedback device for a control loop where corrections are made to the proppant flow rate by the control system in order achieve a setpoint concentration. In the control system described in U.S. Pat. No. 4,779,186, a densitometer is employed to adjust the speed of a screw conveyor regulating the proppant delivery rate into the base treatment fluid.

U.S. Patent Application Publication No. 2015/0060065 A1 describes a control system, associated methodology, and apparatus for implementation of an eductor-mixer technique to provide the capability to inject and meter proppant material into a non-aqueous fracturing fluid stream. The system utilizes a solids-conveying liquid eductor instead of a conventional auger to mix and accelerate proppant within the main fracturing liquid stream. The control system utilizes at least one valve for controlling the flow of proppant from one or more pressurized proppant reservoir into the eductor; thereby mixing the material with the motive stream. Gas and/or liquid is fed to the top of the proppant reservoir to control the pressure inside the proppant reservoir. Modifying the pressure inside the proppant reservoir extends the range of achievable proppant flow rates from the reservoir into the eductor.

Direct and accurate measurement of proppant concentration is quite important for proper control of the system described above. Therefore, the densitometer is a crucial instrument during operation. With ultra-light weight proppant (ULWP), measurement by this important instrument is negated by the relatively similar density to the carrier fluid, leaving accurate concentration control impossible.

To overcome the deficiencies in the related art, the present invention provides the application of a non-nuclear optical device using near-infrared (NIR), visible (Vis), or ultraviolet (UV) spectral ranges for the specific use in the detection and measurement of proppant blended into a fracturing fluid stream and thereby used as a means to regulate proppant concentration through its integration into a control system. The NIR/Vis/UV-based device addresses specific needs in the measurement of ultra-light weight proppant (with densities close to a specific gravity of 1), which is undetectable by conventional nuclear densitometers. The eliminated compliance and associated regulatory cost required for operating a nuclear device is also a benefit that can be applied to more typical sand proppant applications (i.e. proppants with a specific gravity greater than ~2).

Although NIR/Vis/UV based devices have been utilized in the oilfield, the focus has been on property monitoring for chemical characteristics and movement of fluid. In U.S. Patent Application Publication Nos. 2010/022435, 2014/061449, and 2015/015884 fluid interactions with NIR, visible, and ultraviolet radiation is used to monitor molecular characteristics rather than proppant concentration control. For example, U.S. Patent Application Publication No. 2011/0214488 describes the use of NIR for detection of fluorescent nanoparticle-based tracer. While the use of a spectrometer is used in detection tracking of fracturing fluid movement, the art is non-related in application to proppant concentration control.

SUMMARY OF THE INVENTION

The present invention provides an optical device to measure the concentration of proppant concentration in a fracturing fluid, wherein the carrier fluid is preferably liquid carbon dioxide. More specifically, this system employs an instrument that uses near-infrared, visible, or ultra-violet light for detection, measurement, and control of proppant in a pressurized flowing fracturing fluid stream by the attenuation (by absorption and scattering) or scattering of light.

In one aspect of the invention, a feedback control method for adjusting the proppant concentration in a fracturing fluid that is utilized in stimulation of an underground formation is provided. The method includes supplying proppant or proppant slurry from proppant reservoir to a fluid stream; combining the proppant or proppant slurry with the fluid forming a fracturing fluid containing proppant and measuring the concentration of the proppant in said fracturing fluid downstream by a concentration meter, wherein the concentration meter is photometer/nephelometer device utilizing optical light; providing a feedback signal to a computer; and changing the concentration of the fracturing fluid based on the feedback signal of the concentration meter.

In another aspect of the invention, a feedback control method for adjusting the proppant concentration in a fracturing fluid that is utilized in stimulation of an underground formation is provided. The method includes supplying proppant or proppant slurry from a sealed, pressurized proppant reservoir to a motive fluid stream wherein the pressurized proppant reservoir is in a position to supply the proppant slurry to at least one eductor, supplying the motive fluid flow of liquefied gas at pressure between about 150 to 400 psig to the at least one eductor, wherein the liquefied gas is mixed with proppant or proppant slurry to form a fracturing fluid containing proppant and measuring a concentration of the proppant in said fracturing fluid downstream by a photometer/nephelometer device; providing a signal to a computer from the photometer/nephelometer device; changing the concentration of the fracturing fluid based on the reading of the photometer/nephelometer device by sending a signal from the computer to route a pressurized fluid to the proppant reservoir thereby manipulating the pressure in said proppant reservoir or by sending a signal to a control valve disposed between the eductor and the proppant reservoir, and control the proppant concentration from about 0.1 to 10 lbs/gal of proppant in the fracturing fluid.

DETAILED DESCRIPTION OF THE INVENTION

Measurement of concentration of proppant in a liquid carbon dioxide carrier of a fracturing fluid is important for the propping up the fissures in a subterranean formation. Since near-infrared, visible, and ultraviolet light is more susceptible to attenuation and scattering by a solid in solution, and given that ultra-low weight proppant has a specific gravity close to that of the liquid carbon dioxide, the use of a NIR/Vis/UV photometer is essential in detection these low density materials. As utilized in the present invention, ultra-low weight proppant will be understood to be a proppant having a specific gravity in the range of less than 2 or a density of less than 16.7 lbs/gal.

It is possible to detect and measure solids concentration in a fluid through the use of an absorbance photometer, a device used to measure the attenuation of light by a photodetector. Since molecular absorption and scattering of NIR/Vis/UV light can occur in the fluid, transfer through a treatment fluid is dependent on the optical properties (reflectivity, refractive index, structure, density) and molecule interactions of:

the carrier fluid (water, liquefied gas),
dissolved & undissolved additives (polymers, salts), &
the suspended particulate (sand, thermoplastic proppant)

Figure 1A:
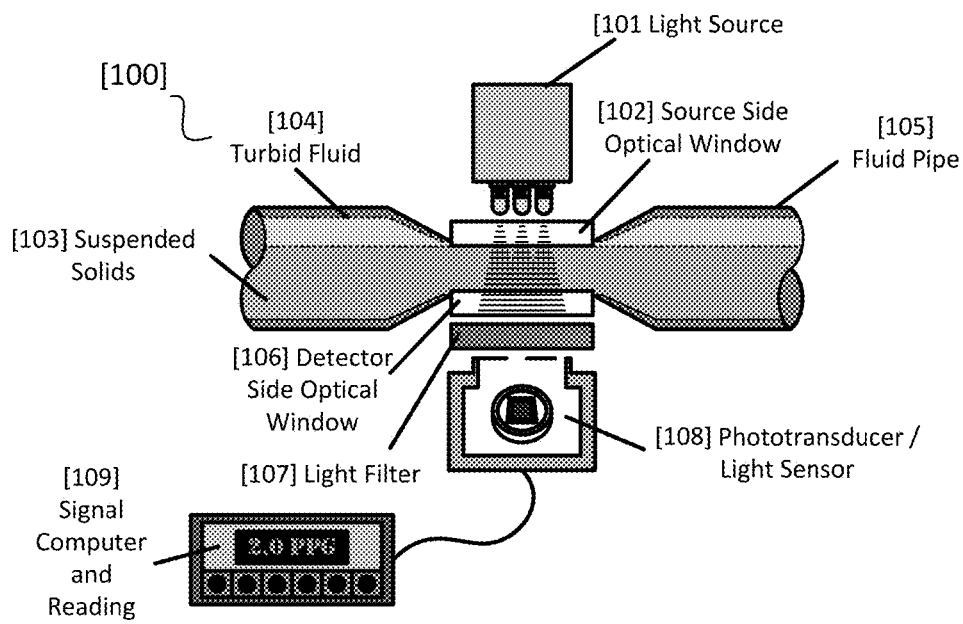
FIG. 1A is a drawing illustrating the operation of a photometer and, FIG. 1B, a nephelometer in the detection and measurement of proppant in a fracturing fluid.

For NIR/Vis/UV light, transfer through treatment piping wall is impossible and through the treatment fluid can be limited. The photometers 100 require "fluid-wetted" windows for light to pass through from the light source to the detector. For example, and with reference to FIG. 1A, large diameter piping 105 devices may be designed to resemble a "pinched pipe" to provide a short optical path length for detection as shown by the shortened distance between the source side optical window 102 and the detector side optical window 106. These waves are detected by a phototransducer or light sensor 108 and converted in a program logic controller (PLC) to a specific reading of concentration.

Figure 1B:
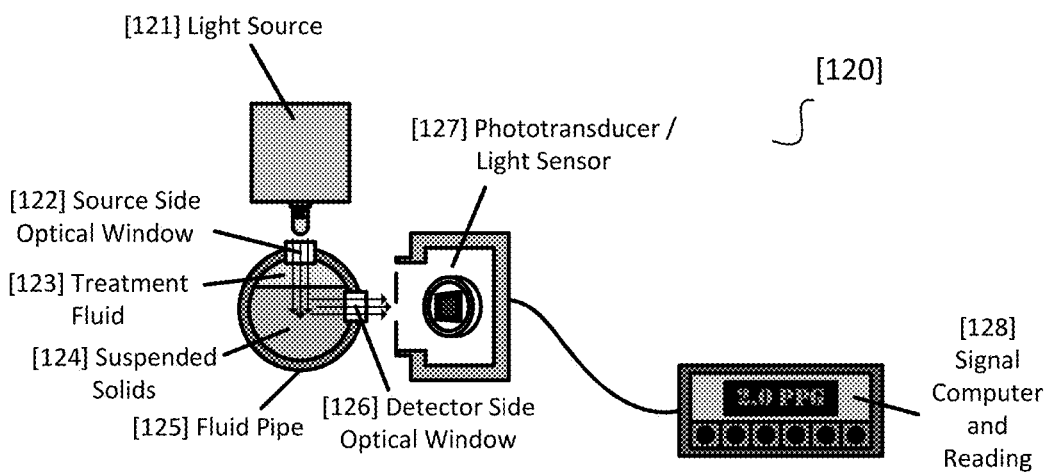

Solids concentration can also be measured through light scattering with a device such as a nephelometer 120. The deflected light is the result of particles in transparent fluid like undissolved solids, emulsions (e.g. oil droplets in water), and bubbles. Since suspended solids 124 are the main cause of scattered light, effects of dissolved material is negated. The components of a nephelometer 120, and as illustrated in FIG. 1B are similar to a absorbance photometer 100, except the detector 127 is placed at specific angle to incident of light (generally 90°). Nephelometers are more sensitive to particle size, concentration, shape, and reflectivity; and therefore requiring calibration to individual particulate types since scattering is dependent on particle characteristics. Furthermore, if particulate 124 is not conducive to scattering (but rather absorption) this can challenge detection with this method.

Figure 2:
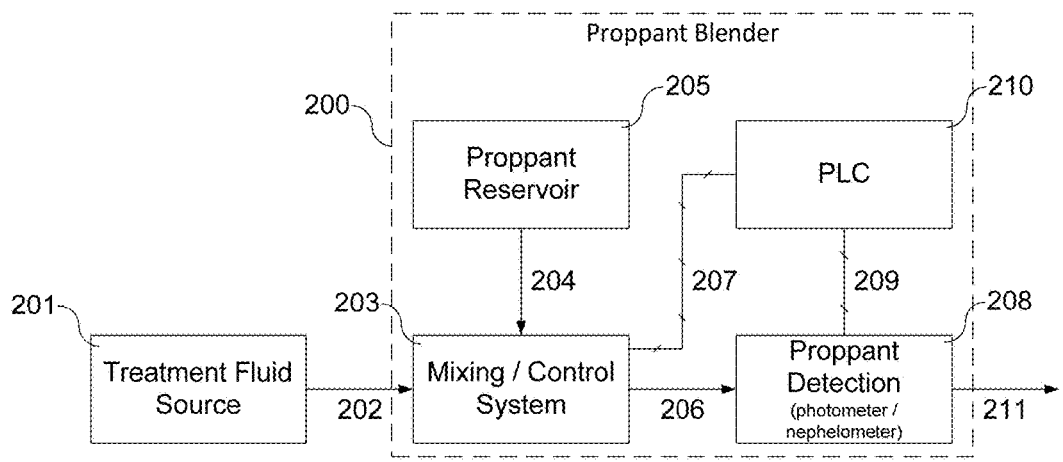
FIG. 2 is a block diagram depicting the application of a photometer/nephelometer as a feedback device for a proppant concentration control system.

In an exemplary embodiment, the photometer/nephelometer is employed as a feedback device for a proppant concentration control system. FIG. 2 illustrates a process outline for the manner of integrating of such a particle detection device into a proppant blender. In a basic proppant blending operation, the treatment fluid 201 is directed towards a proppant blender 200 inclusive of proppant storage or reservoir 205, a mixing system 203 that blends proppant into the treatment stream 206, a process controller 210, and a proppant detection/feedback device 208. The process controller 210 and feedback device 208 are used to adjust the proppant addition rate in the mixing system 203 to provide a set concentration value.

The particle detection device 208 sends an input signal 209 to a process controller 210. The controller 210 in turn, outputs a signal 207 to a control system 203 so as to regulate the proppant flow from reservoir 205 into a treatment stream 206.

Figure 3:
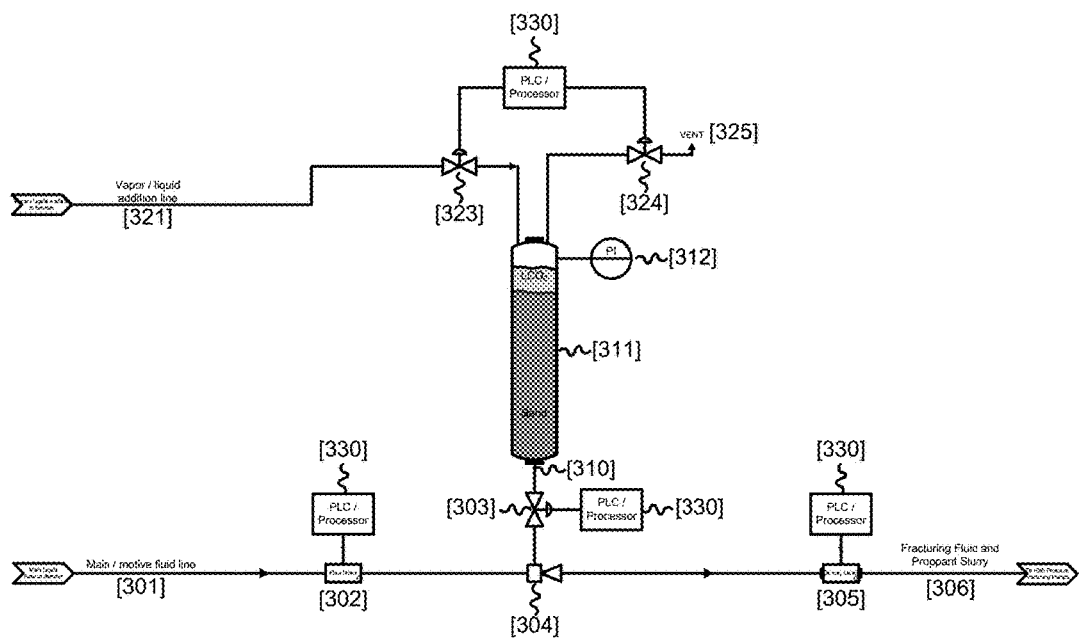
FIG. 3 is a schematic depicting an embodiment of a proppant blender system utilizing an eductor and a NIR/Vis/UV optical device for measuring proppant concentration. The device is used as feedback for a control system comprising of a control valve disposed between the proppant reservoir and main treatment fluid piping, and control valves for managing the pressure in the proppant reservoir during proppant injection.

FIG. 3 shows a proppant addition apparatus similarly described by the document U.S. Published Patent Application U.S. 2015/0060065 A1, which is hereby incorporated by reference in its entirety. Motive fluid or clean liquid carbon dioxide stream enter the system through upstream piping 301 and passes through an eductor 304. The pressure of the motive fluid is about 150 to 400 psig. As liquids pass through the converging nozzle of the eductor, potential energy is converted into kinetic energy resulting in a high velocity jet flow. This change in energy results in a localized decrease in static pressure that creates suction within the body of the eductor. This suction allows material from the reservoir 311 to be drawn into the eductor and entrained by the fluid ($LCO_2$, etc.). The eductor serves a dual purpose: mixing within the nozzle as well as drawing material into the fluid to ensure intimate mixing. The combined clean fluid and material is then sent to high pressure pumpers via the upstream piping 306. The rate of flow of material entering the outlet of the reservoir 310 is controlled by use of a combined control valve 303 and reservoir pressure. The pressure in the reservoir is sensed by pressure indicator 312. The pressure is controlled through the use of a pressurized fluid 321 regulated by control valve 323 and vent 325 regulated by control valve 324. A processor 330 is used to output the control signal to said control valves 303, 323, 324. The processor 330 is typically a single unit, shown in the figure at several locations to simplify the illustration. An NIR device such as photometer/nephelometer 305, whose signal is used as input for the processor 130, is a feedback device for controlling the positioning of flow control valve 303 to control the proppant concentration in a range from about 0.1 to 10 lbs/gal.

EXAMPLE

To demonstrate the efficacy for ultra-light weight proppant detection with NIR photometry, a laboratory experiment was set up using NIR emmiting LED's, a NIR sensitive phototransducer, and vials of suspended plastic ULW proppant. The vials contained various concentrations of ULWP from 0 to 1 ppa (or ~2.5 ppa sand equivalent) with water as a suspension fluid. Specifically, four vials at concentrations of 0, 0.25, 0.5, and 1.0 ppa were prepared. The ULW proppant tested was a thermoplastic developed by Sun Drilling under the trade name FracBlack HT. The material has a specific gravity close to that of water and $CO_2$, ~1.054 or 8.8 lbs/gal.

A 850 nm monochromatic, NIR-emitting LED was selected to minimize the light interactions with the water in the vials. The transmission and scattering of light was measured using current generated from a photodiode. The current was measured with resistor shunt and voltmeter.

Figure 4:
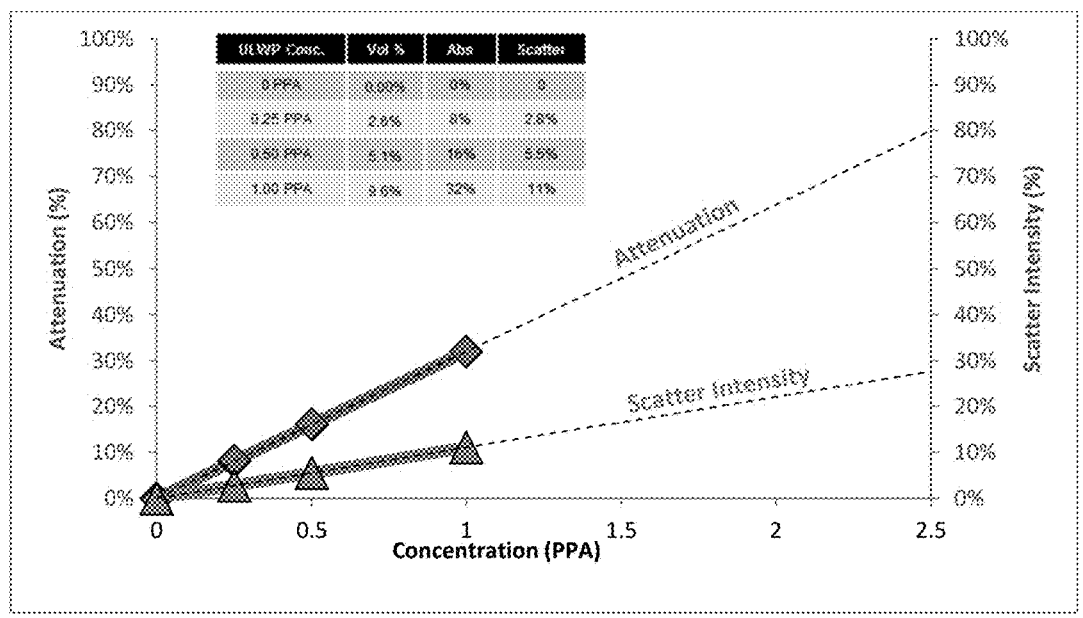
FIG. 4 is a plot that illustrates the measurement of NIR light attenuation and scattering by the presence of ultra-light weight proppant suspended in a fluid at various concentration.

A vial of proppant free water (0 ppa) was used to calibrate reading from the voltmeter. The voltage was then measured using the various ULW proppant laden fluids at 0.25, 0.75, and 1 ppa. Measurement was taken with the detector position at parallel (mimicking attenuation) and perpendicular (mimicking scattering) to the light source. The results are shown in FIG. 4. The concentration of ULWP in the vials affects the scattering and attenuation of the light source and therefore can be used to detect and infer a concentration of ULWP in the fluid.

While the invention has been described in detail with reference to specific embodiments thereof, it will become apparent to one skilled in the art that various changes and modifications can be made, and equivalents employed, without departing from the scope of the appended claims.

What is claimed is:

1. A feedback control method for adjusting the proppant concentration in a fracturing fluid that is utilized in stimulation of an underground formation, comprising:
   supplying proppant or proppant slurry from proppant reservoir to a fluid stream;
   combining the proppant or proppant slurry with the fluid forming a fracturing fluid containing proppant and measuring the concentration of the proppant in said fracturing fluid downstream by a concentration meter, wherein the concentration meter is a photometer/nephelometer device utilizing optical light;
   providing a feedback signal to a computer; and
   changing the concentration of the fracturing fluid based on the feedback signal of the concentration meter.

2. The feedback control method of claim 1, wherein the photometer/nephelometer device utilizes near-infrared light.

3. The feedback control method of claim 1, wherein the photometer/nephelometer device utilizes visible light.

4. The feedback control method of claim 1, wherein the photometer/nephelometer device utilizes ultraviolet light.

5. The feedback control method of claim 1, wherein the photometer/nephelometer device measures the amount of light attenuated by the proppant in the fracturing fluid.

6. The feedback control method of claim 1, wherein the photometer/nephelometer device measures the amount of light scattered by the proppant in the fracturing fluid.

7. The feedback control method of claim 1, wherein the signal from the photometer/nephelometer device is transformed into a concentration in a PLC.

8. The feedback control method of claim 7, wherein the PLC is employed to manipulate a mixing/control system to arrive at a desired concentration.

9. A feedback control method for adjusting the proppant concentration in a fracturing fluid that is utilized in stimulation of an underground formation, comprising:
   supplying proppant or proppant slurry from a sealed, pressurized proppant reservoir to a motive fluid stream wherein the pressurized proppant reservoir is in a position to supply the proppant slurry to at least one eductor;
   supplying a motive fluid flow of liquefied gas at pressure between about 150 to 400 psig to the at least one eductor, wherein the liquefied gas is mixed with proppant or proppant slurry to form a fracturing fluid containing proppant and measuring a concentration of the proppant in said fracturing fluid downstream by a photometer/nephelometer device;

providing a signal to a computer from the photometer/nephelometer device;

changing the concentration of the fracturing fluid based on the reading of the photometer/nephelometer device by sending a signal from the computer to route a pressurized fluid to the proppant reservoir thereby manipulating the pressure in said proppant reservoir or by sending a signal to a control valve disposed between the eductor and the proppant reservoir, and control the proppant concentration from about 0.1 to 10 lbs/gal of proppant in the fracturing fluid.

10. The feedback control method of claim 9, wherein the photometer/nephelometer device utilizes near-infrared light.

11. The feedback control method of claim 9, wherein the photometer/nephelometer device utilizes visible light.

12. The feedback control method of claim 9, wherein the photometer/nephelometer device utilizes ultraviolet light.

13. The feedback control method of claim 9, wherein the photometer/nephelometer device measures the amount of light attenuated by the proppant in the fracturing fluid.

14. The feedback control method of claim 9, wherein the photometer/nephelometer device measures the amount of light scattered by the proppant in the fracturing fluid.

15. The feedback control method of claim 9, wherein the signal from the photometer/nephelometer device is transformed into a concentration in the computer.

16. The feedback control method of claim 15, wherein the computer is employed to manipulate a mixing/control system to arrive at a desired concentration.

* * * * *